United States Patent [19]

Bleau et al.

[11] Patent Number: 5,792,086
[45] Date of Patent: Aug. 11, 1998

[54] NEUROPHYSIOLOGICALLY DESIGNED KNEE ORTHOSIS WITH THREE DIMENSIONAL JOINT

[75] Inventors: Jean-Claude Bleau, Boucherville; Kurt Gauss, Montréal; Rony Herrera, Montréal; Vassilios Vardaxis, Montréal; Tuong Ngoc Huynh, St-Hubert, all of Canada

[73] Assignee: Les Équipements Médicus Ltée, Montréal, Canada

[21] Appl. No.: 641,722

[22] Filed: May 2, 1996

[30] Foreign Application Priority Data

Feb. 13, 1996 [CA] Canada ................... 2169435

[51] Int. Cl.$^6$ ................................................ A61F 5/60
[52] U.S. Cl. ................................................ 602/26; 602/16
[58] Field of Search .................................. 602/5, 16, 23, 602/26

[56] References Cited

U.S. PATENT DOCUMENTS

| | | |
|---|---|---|
| 1,390,915 | 9/1921 | Loth . |
| 3,779,654 | 12/1973 | Horne . |
| 3,902,482 | 9/1975 | Taylor . |
| 4,361,142 | 11/1982 | Lewis et al. . |
| 4,463,751 | 8/1984 | Bledsoe . |
| 4,723,539 | 2/1988 | Townsend . |
| 4,751,920 | 6/1988 | Mauldin et al. ............... 602/16 |
| 4,773,404 | 9/1988 | Townsend ................... 602/26 X |
| 4,886,054 | 12/1989 | Castillo et al. ............... 602/26 |
| 4,940,044 | 7/1990 | Castillo ........................ 602/16 |
| 5,009,223 | 4/1991 | Defonce ........................ 128/80 |
| 5,022,391 | 6/1991 | Weidenburner ............... 602/16 |
| 5,063,916 | 11/1991 | France et al. ................ 602/26 |
| 5,107,824 | 4/1992 | Rogers et al. . |
| 5,131,385 | 7/1992 | Kuehnegger et al. ......... 602/26 X |
| 5,230,696 | 7/1993 | Silver et al. . |
| 5,277,698 | 1/1994 | Taylor . |
| 5,286,250 | 2/1994 | Meyers et al. . |
| 5,302,169 | 4/1994 | Taylor . |
| 5,542,774 | 8/1996 | Hey .............................. 602/16 X |
| 5,632,725 | 5/1997 | Silver et al. ................. 602/16 X |

FOREIGN PATENT DOCUMENTS

WO 9503013  2/1995  WIPO .

*Primary Examiner*—Richard J. Apley
*Assistant Examiner*—Denise Pothier
*Attorney, Agent, or Firm*—Robic

[57] ABSTRACT

A knee orthosis in which the lateral and medial hinges are articulated asymmetrically. The medial hinge, having a first variable axis of rotation, has a first pair of parallel concentric shells in the shape of the segment of a sphere defining a first opening between them, fastened to the medial portion of the thigh cuff, and three rivets, forming a first equilateral triangle having a center coincident with the first variable axis of rotation, fastened to each shell. The medial hinge also has a first shell in the shape of a segment of a sphere designed to be inserted into the first opening, fastened to the medial portion of the shank cuff and three grooves to receive the three rivets. The lateral hinge, having a second variable axis of rotation, has a second pair of parallel concentric shells in the shape of a segment of a sphere defining a second opening between the shells, fastened to the lateral portions of the thigh cuff, and three rivets, forming a second equilateral triangle having a center coincident with the second variable axis of rotation, fastened to each shell. The lateral hinge also has a second shell in the shape of a segment of the sphere designed to be inserted into the second opening, fastened to the lateral portion of the shank cuff and three grooves to receive the three rivets. The medial hinge and the lateral hinge have concavities opposite each other and facing the knee, in order to account for the variable axis of rotation of the knee joint within the anatomical boundaries of the knee.

9 Claims, 6 Drawing Sheets

NEUROPHYSIOLOGICALLY DESIGNED KNEE ORTHOSIS WITH THREE DIMENSIONAL JOINT

FIELD OF THE INVENTION

The present invention is concerned with an improved orthotic device for a lower limb.

DESCRIPTION OF THE PRIOR ART

A variety of knee orthoses and joints for knee orthoses have been proposed to control or aid movement of the knee after an injury or an operation, to aid in the healing of a damaged knee or to protect the knee while engaging in sports activities, which purport to accurately mimic the movement of the knee joint during flexion and extension of the leg. More particularly, some of these orthoses and joints, when the leg is extended, have their rotation axes coincident with the wearer's condyles, but the axes of rotation do not remain coincident throughout the range of motion.

Furthermore, a number of the recent patents granted in the field refer to the equations of motion published in 1985 by Walker et al, "External Knee Joint Design Based on Normal Motion", in Journal of Rehabilitation Research and Development, Vol. 22, No. 1, pages 9–22 (hereinafter referred to as "WALKER").

In general, reference may be made, for example, to U.S. Pat. No. 5,107,824 (ROGERS et al., 1992), 5,230,696 (SILVER et al., 1993) and 5,286,250 (MEYERS et al., 1994) and the prior art cited therein.

To Applicant's knowledge, none of the existing prior art accurately mimics the complete asymmetric motion of femoral condyles of the knee in relation to the tibia, i.e. flexion and extension, abduction and adduction, internal-external rotation and anterior posterior translation, all of which occur concurrently.

Furthermore, these orthoses and joints do not provide for the migration or pistoning of the orthoses due to the ratcheting motion caused by alternately flexing and extending the leg, which eventually misaligns the axes of rotation of the orthoses with the instantaneous axis of rotation of the knee and may cause further damage, impede motion or impede the healing of an injured knee.

These orthoses do not either provide in their structure for differences in the size of a wearer's leg and thus are not properly adjustable.

SUMMARY OF THE INVENTION

It is a first object of the invention to provide a physiologically designed improved knee orthosis with a three-dimensional axis which accurately tracks the anatomical motion of the knee during flexion and extension of the leg, hereinafter referred to as the "instantaneous axis of rotation", which has a center of rotation inside the anatomical boundaries of the knee. More particularly, it is the first object of the invention to provide a hinge for such an orthosis where the axes of rotation are aligned, when the leg is extended, with the wearer's epicondyles and are coincident and pass through the center of rotation throughout the range of motion.

In accordance with the invention, this first object is achieved with a neurophysiologically designed improved knee orthosis of the type comprising:

a thigh cuff having a medial portion, a lateral portion and an anterior portion;

a shank cuff having a medial portion, a lateral portion and an anterior portion;

a lateral hinge for linking the lateral portion of the thigh cuff to the lateral portion of the shank cuff;

a medial hinge for linking the medial portion of the thigh cuff to the medial portion of the shank cuff;

means to strap the thigh cuff to a wearer's thigh;

means to strap the shank cuff to a wearer's shank;

where:

the lateral hinge has a first variable axis of rotation and comprises:

a first pair of parallel, concentric shells in the shape of a segment of a sphere defining a first opening between them, fastened to one of the lateral portions of the thigh cuff or the shank cuff and having a first, second and third rivets, forming a first equilateral triangle having a center coincident with the first variable axis of rotation, fastened to each shell of the first pair of parallel, concentric shells; and a first shell in the shape of a segment of a sphere designed to be inserted into the first opening, fastened to the other of the lateral portions of the thigh cuff or the shank cuff and having a first, second and third grooves to receive the first, second and third rivets respectively; and the medial hinge has a second variable axis of rotation and comprises:

a second pair of parallel, concentric shells in the shape of a segment of a sphere defining a second opening between the shells, fastened to one of the medial portions of the thigh cuff or the shank cuff and having a fourth, fifth and sixth rivets, forming a second equilateral triangle having a center coincident with the second variable axis of rotation, fastened to each shell of the second pair of parallel concentric shells; and a second shell in the shape of a segment of a sphere designed to be inserted into the second opening, fastened to the other of the medial portions of the thigh cuff or the shank cuff and having a fourth, fifth and sixth grooves to receive the fourth, fifth and sixth rivets respectively, and the medial hinge and the lateral hinge have concavities having concave surface facing the knee and opposite each other.

In use, when the wearer's leg is extended, the first variable axis of rotation and the second variable axis of rotation are coincident and in alignment with the wearer's epicondyles, and when the wearer's leg flexes and extends, the first variable axis of rotation and the second axis of rotation are coincident throughout the range of motion, thereby accurately mimicking the instantaneous axis of rotation of the wearer's knee throughout flexion and extension, abduction and adduction and internal-external rotation and anterior/posterior translation.

It is a second object of the present invention to provide for an improved knee orthosis which prevents migration or pistoning of the knee orthosis along the wearer's leg as the leg is alternately flexed and extended.

In accordance with the invention, this second object is achieved with an improved knee orthosis of the type mentioned above, where the shank cuff further comprises a slidable lower shin cuff. More particularly, the lower shin cuff has an anterior portion having a vertical slot of given length and a tongue fastened to the anterior portion of the shank cuff, slidably inserted in the vertical slot such that the lower shin cuff may slide upwardly or downwardly along the vertical slot.

It is a third object of the invention to provide for an improved knee orthosis which is structurally adjustable to account for legs of different sizes.

In accordance with the invention, this third object is achieved with an improved knee orthosis of the type mentioned above, where the anterior portion of the thigh cuff further comprises an interior and exterior thigh control bars having a first set of cooperating, vertically oriented teeth which can be incrementally opened or closed from a small position to a large position and a first plate to lock the interior and exterior thigh control bars into position and where the anterior portion of the thigh cuff further comprises an interior and exterior shank control bars having a second set of cooperating, vertically oriented teeth which can be incrementally opened or closed from a small position to a large position and a second plate to lock the interior and exterior shank control bars into position.

BRIEF DESCRIPTION OF THE DRAWINGS

The present invention and its advantages will be more easily understood after reading the following non-restrictive description of preferred embodiments thereof, made with reference to the following drawings where.

DESCRIPTION OF A PREFERRED EMBODIMENT OF THE INVENTION

As knee orthoses may be manufactured for right or left legs and the hinges in each of these are mirror images of each other, the following will describe an orthosis for a right leg.

Figure 1:
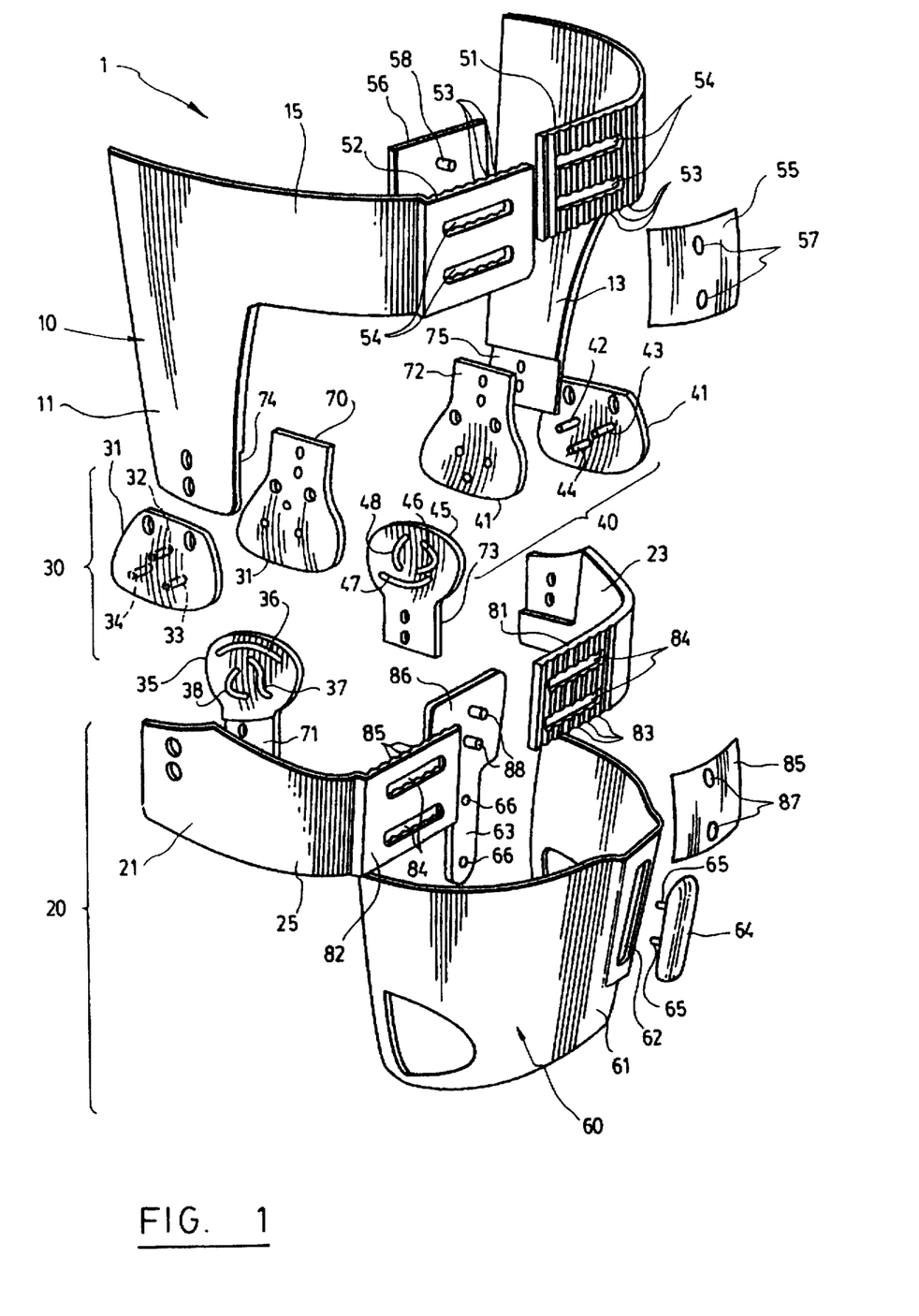
FIG. 1 is an exploded view of a portion of the knee orthosis according to the invention for a right leg.
Figure 2:
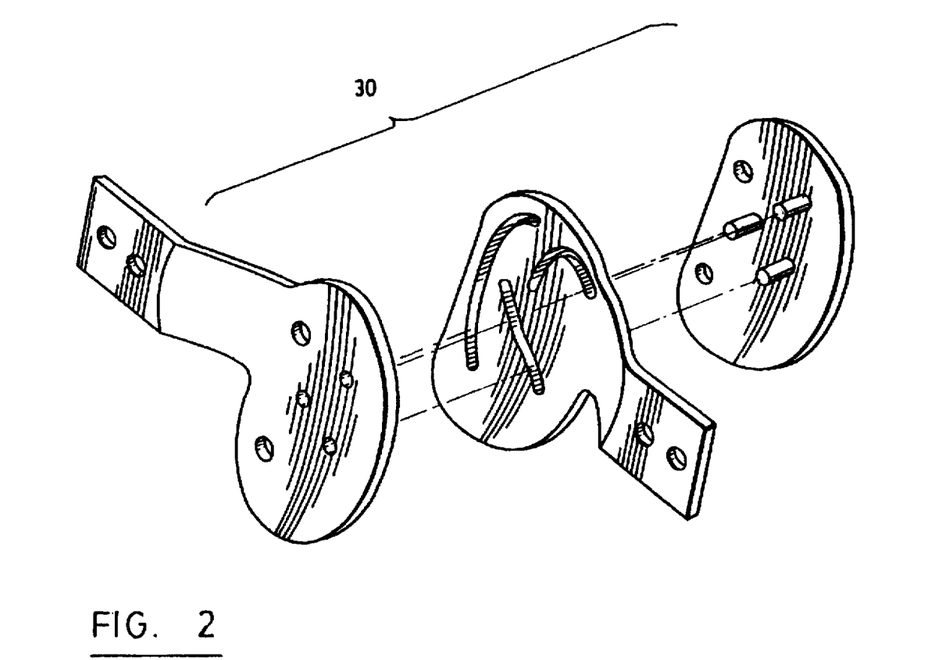
FIG. 2 is an exploded view of the lateral hinge for use in the knee orthosis of FIG. 1.
Figures 3, 5:
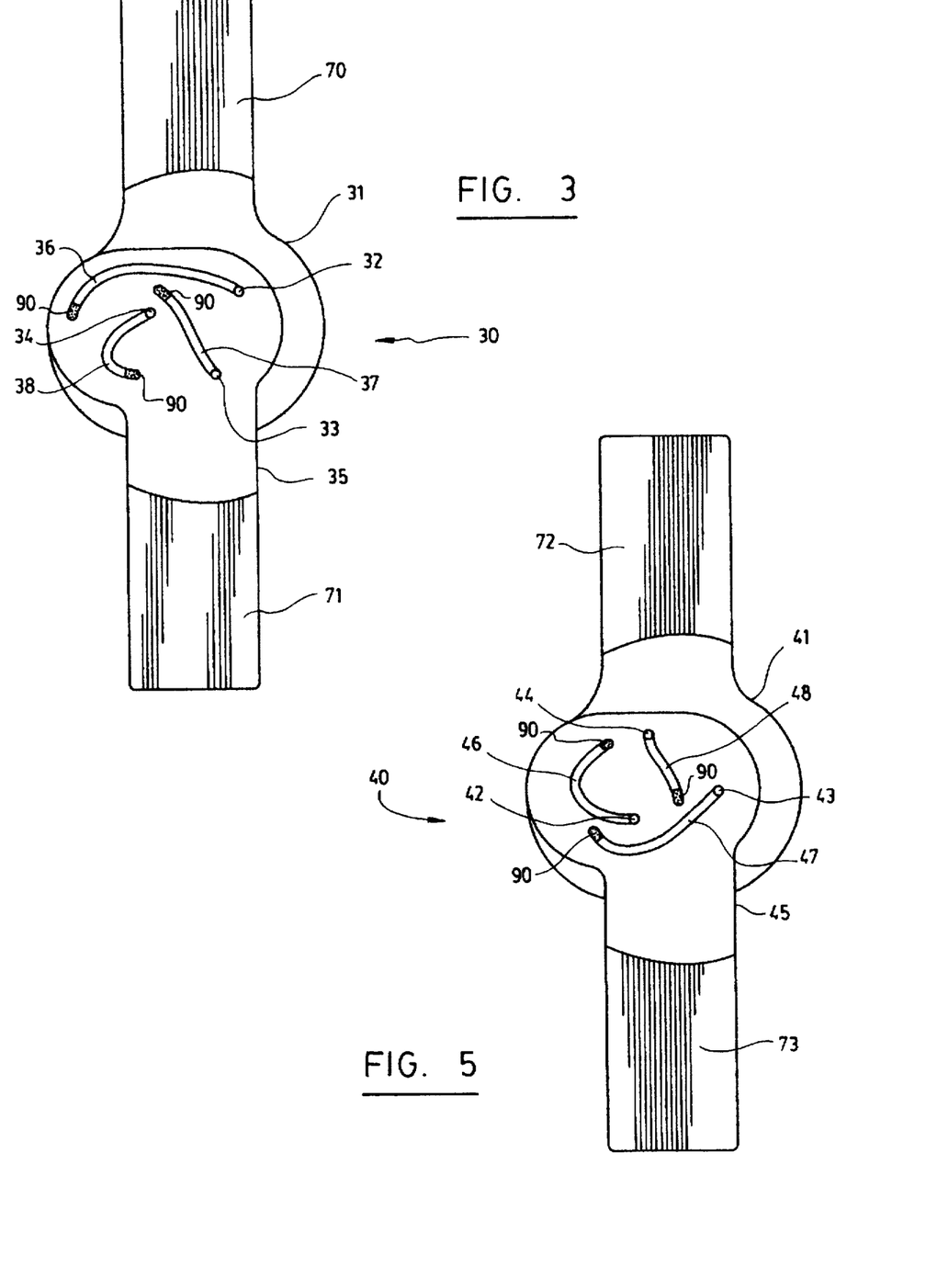
FIG. 3 is a side elevational view of the assembled lateral hinge of FIG. 2.
FIG. 5 is a side elevational view of the assembled medial hinge of FIG. 4.
Figure 4:
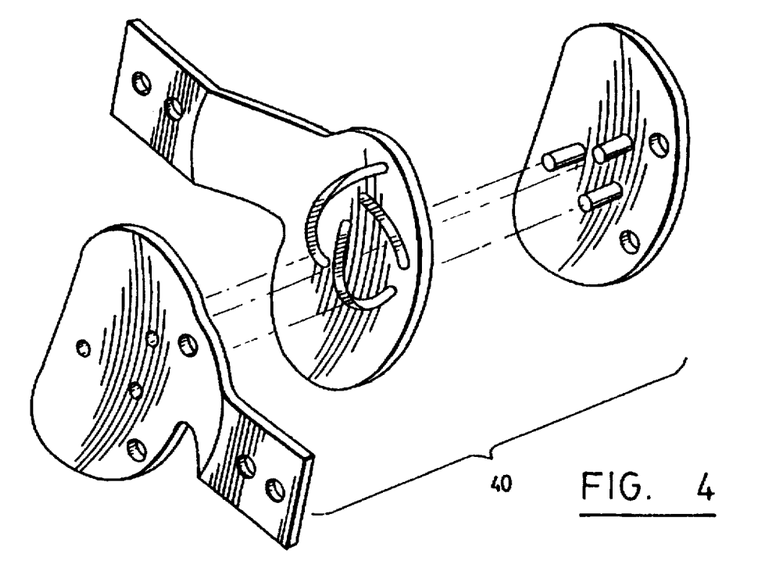
FIG. 4 is an exploded view of the medial hinge for use in the knee orthosis of FIG. 1.

The knee orthosis 1 shown in FIG. 1, preferably made of injection molded plastic, comprises a thigh cuff 10 having a lateral portion 11, a medial portion 13 and an anterior portion 15, a shank cuff 20 having a lateral portion 21, a medial portion 23 and an anterior portion 25, a lateral hinge 30 for linking the lateral portion 11 of the thigh cuff 10 to the lateral portion 21 of the shank cuff 20, a medial hinge 40 for linking the medial portion 13 of the thigh cuff 10 to the medial portion 23 of the shank cuff 20, means to strap the thigh cuff to a wearer's thigh, such as thigh straps 3 and means to strap the shank cuff to a wearer's shank, such as shank straps 5.

The lateral hinge 30, according to the preferred embodiment of the invention, has a first variable axis of rotation and comprises a first pair 31 of parallel, concentric shells in the shape of a segment of a sphere defining a first opening between them. The first pair 31 of shells is fastened to one of the lateral portions 11 or 21 of the thigh cuff 10 or the shank cuff 20. Preferably, the first pair 31 of shells is fastened to the lateral portion 11 of the thigh cuff 10, and is manufactured in an inside and an outside piece, as shown in FIG. 1. The inside shell has an extension 70 which is fastened to the inside 74 of the lateral portion 11 of the thigh cuff. The outside shell is fastened to the inside shell.

A first 32, second 33 and third rivets 34, forming a first equilateral triangle 110 having a center 111 coincident with the first variable axis of rotation, are fastened to each shell of the first pair 31 of shells.

A first shell in the shape of a segment of a sphere 35, designed to be inserted into the first opening, is fastened to the other of the lateral portions 21 or 11 of the thigh cuff 10 or the shank cuff 20. Preferably, the first shell 35 is fastened to the lateral portion 21 of the shank cuff 20 by way of an extension 71. The first shell 35 has first 36, second 37 and third 38 grooves to receive the first 32, second 33 and third 34 rivets respectively.

The medial hinge 40, according to the preferred embodiment of the invention, has a second variable axis of rotation and comprises a second pair 41 of parallel, concentric shells in the shape of a segment of a sphere defining a second opening between them. The second pair 41 of shells is fastened to one of the medial portions 13 or 23 of the thigh cuff 10 or the shank cuff 20. Preferably, the second pair 41 of shells is fastened to the medial portion 13 of the thigh cuff and is manufactured in an inside and an outside piece, as shown in FIG. 1. The inside shell has an extension 72 which is fastened to the inside 75 of the medial portion 13 of the thigh cuff. The outside shell is fastened to the inside shell.

A fourth 42, fifth 43 and sixth 44 rivets, forming a second equilateral triangle 100 having a center 101 coincident with the second variable axis of rotation, are fastened to each shell of the second pair 41 of shells.

A second shell in the shape of a segment of a sphere 45, designed to be inserted into the second opening, is fastened to the other of the medial portions 23 or 13 of the thigh cuff 10 or the shank cuff 20. Preferably, the second shell 45 is fastened to the medial portion 23 of the shank cuff 20 by way of an extension 73. The second shell 45 has fourth 46, fifth 47 and sixth 48 grooves to receive the fourth 42, fifth 43 and sixth 44 rivets respectively.

As shown in FIG. 1, the lateral hinge 30 and the medial hinge 40 have concave surfaces facing the knee and opposite each other in order to maintain the axes of rotation of the hinges aligned with the center of rotation of the knee and within the anatomical boundaries of the knee.

The lateral hinge 30 and the medial hinge 40 were designed based on WALKER's equations of motion. However, those equations have an infinite number of solutions. In order to obtain a workable solution, some of the parameters must be constrained. According to the preferred embodiment of the invention, the hinges 30 and 40 meet the following minimum criteria: the orthosis must be able to flex and extend over 0° to 120°, must allow for at least 10° of internal/external rotation, 5° of varus/valgus movement (adduction/abduction) and 6 mm of anterior/posterior translation. These are mean figures for normal motion of the knee joint and, as is well known, all of the above movements occur concurrently and are not linearly incremental throughout the range of motion.

In order to further constrain the design parameters, a three rivet-and-slot system was chosen over a two rivet-and-slot system as it offered greater stability, smoother movement, increased solidity and greatly reduced the possibility of the hinges locking during flexion/extension. The equilateral triangles obtained for the configuration of the rivets 32, 33, 34 and 42, 43, 44 minimize the surface area of the assembled hinge and permit the alignment of the axes of rotation with the instantaneous axis of rotation of the knee. As well, the hinges must have concavities opposite each other in order to accurately and precisely mimic the movement of the knee. Thus, the curvature of the hinges controls varus/valgus motion as well and internal/external rotation, whereas the shape and length of the grooves controls flexion/extension and anterior/posterior translation. The shapes of the grooves are better shown on FIGS. 2, 3, 4 and 5. It is an important aspect of the invention that each hinge has a distinct set of grooves as the motion on the medial side of the knee is not symmetrical to the motion on the lateral side of the knee.

Figure 6:
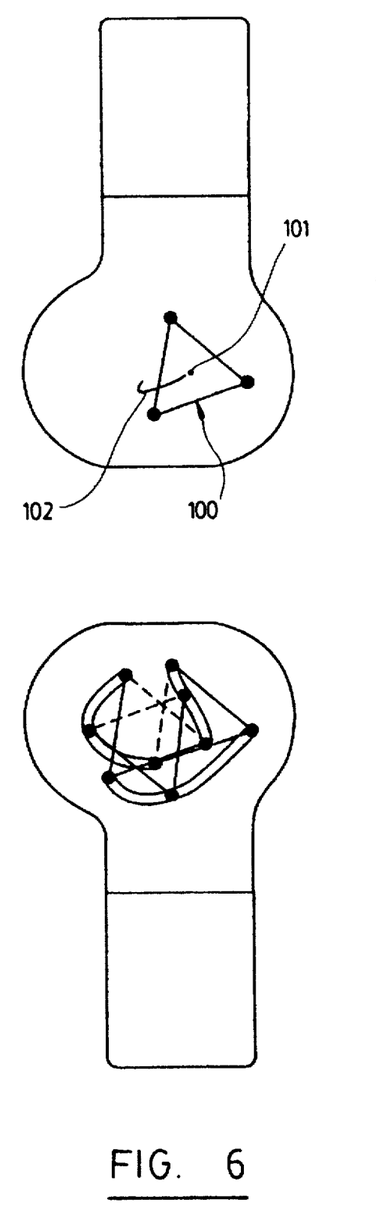
FIG. 6 is a side elevational view of the disassembled medial hinge for use in the knee orthosis of FIG. 1, showing the path of travel of the center of the equilateral triangle mimicking the instantaneous axis of rotation on the medial side of the knee.
Figure 7:
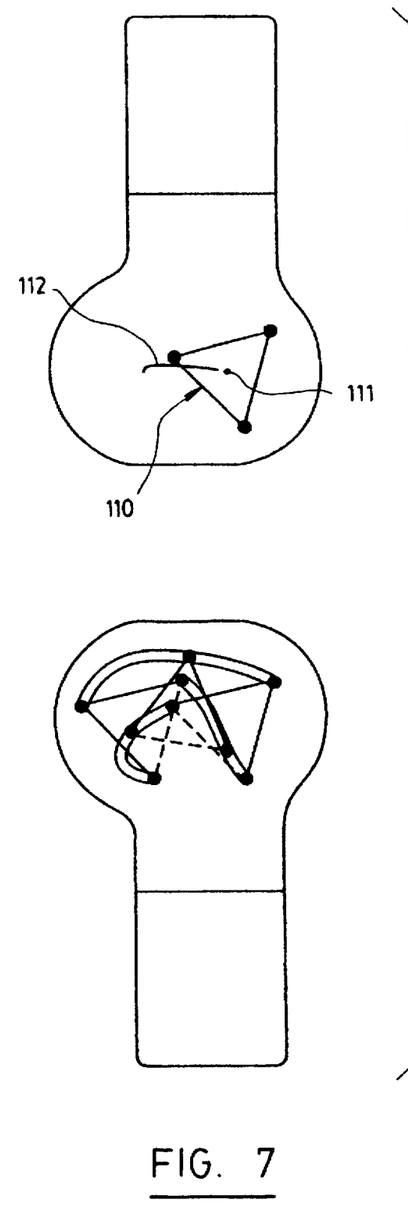
FIG. 7 is a side elevational view of the disassembled lateral hinge for use in the knee orthosis of FIG. 1, showing the path of travel of the center of the equilateral triangle mimicking the instantaneous axis of rotation on the lateral side of the knee.

The knee orthosis according to the invention must be adjusted so that when the wearer's leg is extended, the first variable axis of rotation and the second variable axis of rotation are coincident and in alignment with the wearer's epicondyles, and when the wearer's leg flexes and extends, the first variable axis of rotation and the second axis of rotation are coincident throughout the range of motion and with the axis of rotation of the knee, thus accurately mimicking the instantaneous axis of rotation of the wearer's knee throughout flexion and extension, abduction and adduction, internal-external rotation and anterior/posterior translation. This movement is better shown on FIGS. 6 and 7, where the center 101, 111 of each equilateral triangle 100, 110 are the second and first axes of rotation, respectively and the relative motion of the centers is indicated by the arrowed lines 112, 102.

To that effect, the thigh cuff 10 further comprises means to adjust the thigh cuff 10 to a wearer's thigh including an interior 51 and exterior 52 controls bars located on the anterior portion 15 of the thigh cuff 10. The interior 51 and exterior 52 controls bars include a first set of cooperating, vertically oriented teeth 53, which can be incrementally opened or closed from a small position to a large position. The interior 51 and exterior 52 control bars also preferably include a pair of horizontal slots 54. The interior 51 and exterior 52 control bars may be locked into position through the use of at least one plate 55 having two holes 57 corresponding to the horizontal slots 54, and screws (not shown) to fasten the plate 55 securely to the anterior portion of the thigh cuff 10. Advantageously, a second plate 56 having pins 58 corresponding to the two holes 57 may be locked to the plate 55 by screwing the pins 58 into the holes 57. Furthermore, in order to evenly distribute the force present at the interior 51 and exterior 52 control bars, the plate 55 is preferably cambered.

In addition, the shank cuff 20 further comprises means to adjust the shank cuff 20 to a wearer's shank including an interior 81 and exterior 82 shank control bars located on the anterior portion 25 of the shank cuff 20. The interior 81 and exterior 82 control bars preferably include a second set of cooperating, vertically oriented teeth 83, which can be incrementally opened or closed from a small position to a large position. The interior 81 and exterior 82 control bars also include a pair of horizontal slots 84. The interior 81 and exterior 82 control bars may be locked into position through the use of at least one plate 85 having two holes 87 corresponding to the horizontal slots 84, and screws (not shown) to fasten the plate 85 securely to the anterior portion 25 of the shank cuff 20. Advantageously, a second plate 86 having pins 88 corresponding to the two holes 87 may be locked to the plate 85 by screwing the pins 88 into the holes 87. Preferably, the plate 85 is cambered to evenly distribute the force present at the interior 81 and exterior 82 control plates.

Figure 8:
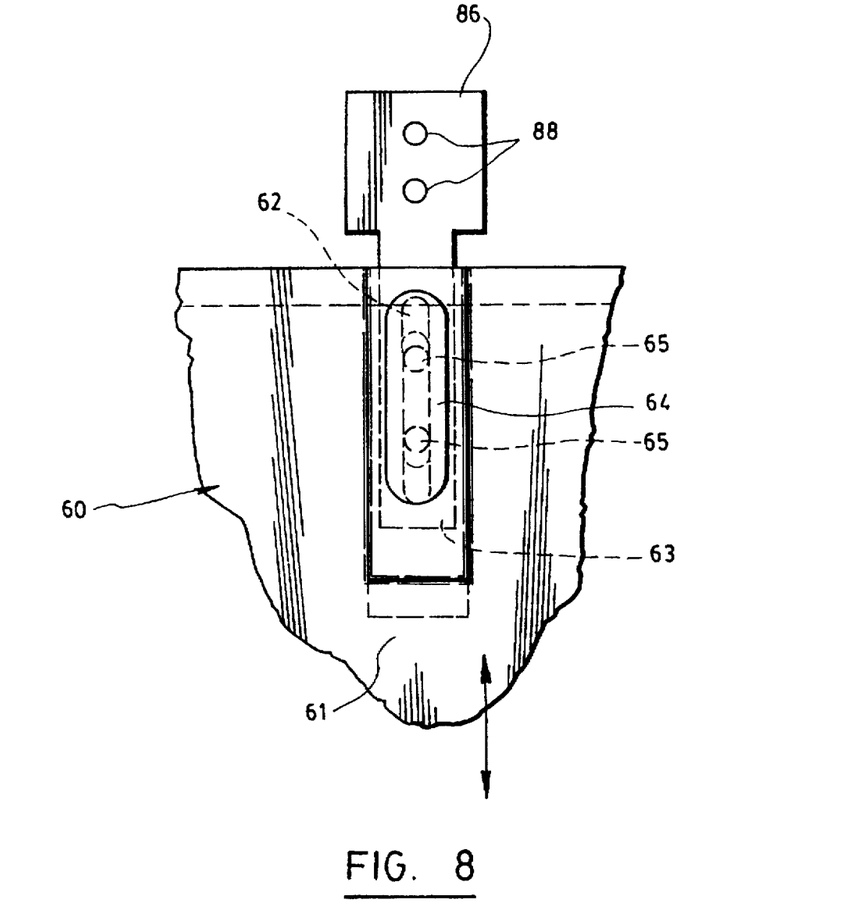
FIG. 8 is a front elevational view of the shin cuff according to the invention.
Figure 9:
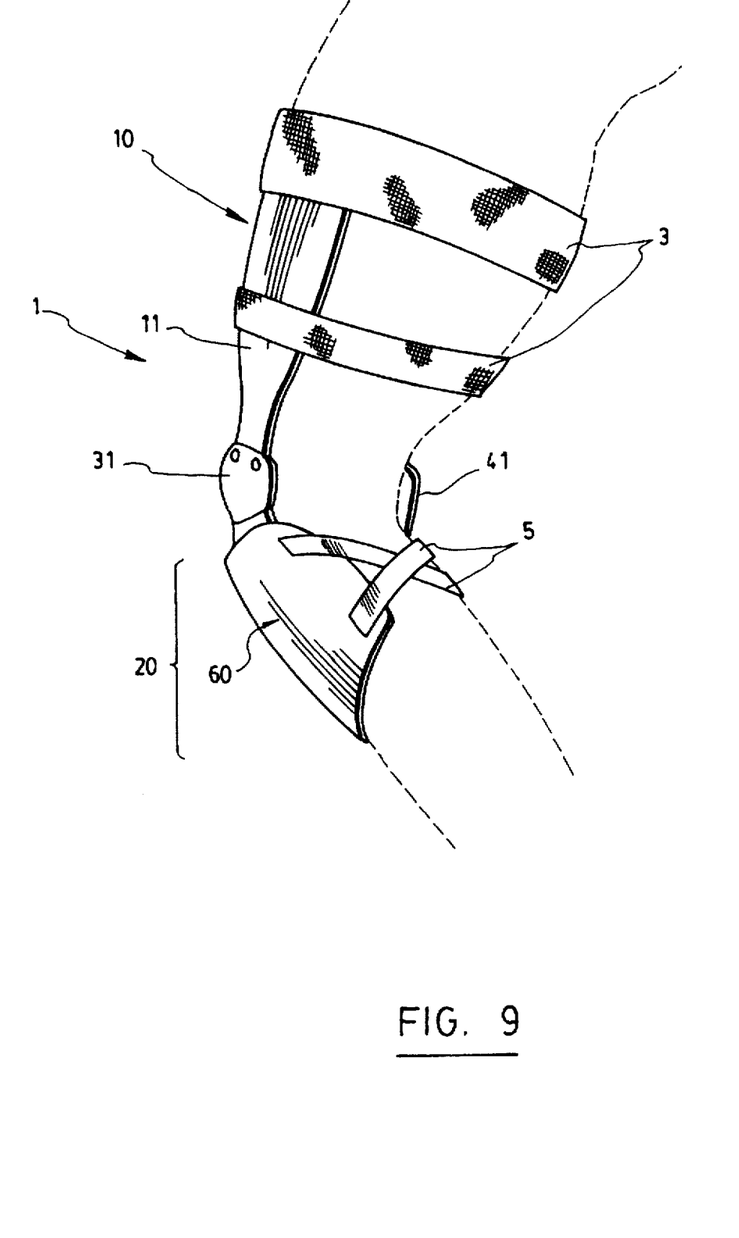
FIG. 9 is a back perspective view of the knee orthosis according to the invention, showing the means to strap the thigh cuff and the shank cuff to a wearer's leg.

One of the problems associated with knee orthoses is the migration or pistoning of the orthosis due to the ratcheting motion caused by alternately flexing and extending the knee. In order to remedy this problem, the knee orthosis 1 according to the invention is provided with a slidable lower shin cuff 60 on the shank cuff 20. The lower shin cuff has an anterior portion 61 having a vertical slot 62 of given length and a tongue 63, fastened to the anterior portion 25 of the shank cuff. Preferably, this tongue is an extension of the plate 86. The tongue 63 is inserted in the vertical slot 62 such that the lower shin cuff 60 may slide upwardly or downwardly along the vertical slot 62, as better seen on FIG. 8. Preferably, a cap 64 is fastened to the tongue 63 to hide the vertical slot 62, and is provided with pins 65 aligned with holes 66 in the tongue 63.

The slidable lower shin cuff 60 is most efficient when the anterior portion 25 of the shank cuff 20 rests on the tibial tuberosity, which is the area on the shank which moves the least during flexion and extension. Thus, when the wearer flexes and extends, the skin on the anterior of the shank may freely stretch so that the relative movement of the tongue 63 with respect to the slot 62 is approximately 1 cm.

Furthermore, the knee orthosis 1 will be most stable when the lateral portion 11 of the thigh cuff 10 rests mainly on the vastus lateralis of the wearer's thigh, which is the muscle which changes least in aspect during flexion and extension and offers a stable point to locate the knee orthosis 1 to a wearer.

In some cases, it is desirable to limit the range of motion of the knee, particularly to protect damaged ligaments or to aid in healing. To that effect, stops, 90 preferably made of nylon or soft rubber, may be mounted in the first 36, second 37, third 38, fourth 46, fifth 47 and sixth 48 slots.

It must also be understood that only the basic structural elements of the knee orthosis have been described. Further elements such as padding and straps to strap the knee orthosis to a wearer have been omitted for purposes of clarity.

Although the present invention has been explained hereinabove by way of a preferred embodiment thereof, it should be pointed out that any modifications to this preferred embodiment within the scope of the appended claims is not deemed to alter or change the nature and scope of the present invention.

What is claimed is:

1. A knee orthosis of the type comprising:

a thigh cuff having a medial portion, a lateral portion and an anterior portion;

a shank cuff having a medial portion, a lateral portion and an anterior portion;

a lateral hinge for linking said lateral portion of said thigh cuff to said lateral portion of said shank cuff;

a medial hinge for linking said medial portion of said thigh cuff to said medial portion of said shank cuff;

means to strap said thigh cuff to a wearer's thigh;

means to strap said shank cuff to a wearer's shank; wherein said lateral hinge has a first variable axis of rotation and comprises:

a first pair of parallel, concentric shells in the shape of a segment of a sphere defining a first opening between said shells, said first pair of parallel, concentric shells being fastened to one of said lateral portion of said thigh cuff and said shank cuff and having first, second and third rivets forming a first equilateral triangle having a center coincident with said first variable axis of rotation, said rivets being fastened to each shell of said first pair of parallel, concentric shells; and a first shell in the shape of a segment of a sphere designed to be inserted into said first opening, said first shell being fastened to the other of said lateral portion of said thigh cuff and said shank cuff and having first, second and third grooves to receive said first, second and third rivets respectively; and said medial hinge has a second variable axis of rotation and comprises:

a second pair of parallel, concentric shells in the shape of a segment of a sphere defining a second opening between said shells, said second pair of parallel, concentric shells being fastened to one of said medial portion of said thigh cuff and said shank cuff and having fourth, fifth and sixth rivets forming a second equilateral triangle having a center coincident with said second variable axis of rotation, said rivets being fastened to each shell of said second pair of parallel, concentric shells; and a second shell in the shape of a segment of a sphere designed to be inserted into said second opening, said second shell being fastened to the other of said medial portion of said thigh cuff and said shank cuff and having fourth, fifth and sixth grooves to receive said fourth, fifth and sixth rivets respectively;

said medial hinge and said lateral hinge having concave surfaces facing the knee and opposite each other, whereby, in use, when the wearer's leg is extended, said first variable axis of rotation and said second variable axis of rotation are coincident and in alignment with the wearer's epicondyles, and when the wearer's leg flexes and extends, said first variable axis of rotation and said second axis of rotation are coincident throughout the range of motion and with the axis of rotation of the knee, thereby accurately mimicking the instantaneous axis of rotation of the wearer's knee throughout flexion and extension, abduction and adduction, internal-external rotation and anterior/posterior translation.

2. A knee orthosis of the type comprising:

a thigh cuff having a medial portion, a lateral portion and an anterior portion;

a shank cuff having a medial portion, a lateral portion and an anterior portion;

a lateral hinge for linking said lateral portion of said thigh cuff to said lateral portion of said shank cuff;

a medial hinge for linking said medial portion of said thigh cuff to said medial portion of said shank cuff;

means to strap said thigh cuff to a wearer's thigh;

means to strap said shank cuff to a wearer's shank; wherein said lateral hinge has a first variable axis of rotation and comprises:

a first pair of parallel, concentric shells in the shape of a segment of a sphere defining a first opening between said shells, said first pair of parallel, concentric shells being fastened to one of said lateral portion of said thigh cuff and said shank cuff and having first, second and third rivets forming a first equilateral triangle having a center coincident with said first variable axis of rotation, said rivets being fastened to each shell of said first pair of parallel, concentric shells; and a first shell in the shape of a segment of a sphere designed to be inserted into said first opening, said first shell being fastened to the other of said lateral portion of said thigh cuff and said shank cuff and having first, second and third grooves to receive said first, second and third rivets respectively; and said medial hinge has a second variable axis of rotation and comprises:

a second pair of parallel, concentric shells in the shape of a segment of a sphere defining a second opening between said shells, said second pair of parallel, concentric shells being fastened to one of said medial portion of said thigh cuff and said shank cuff and having fourth, fifth and sixth rivets forming a second equilateral triangle having a center coincident with said second variable axis of rotation, said rivets being fastened to each shell of said second pair of parallel, concentric shells; and a second shell in the shape of a segment of a sphere designed to be inserted into said second opening, said second shell being fastened to the other of said medial portion of said thigh cuff and said shank cuff and having fourth, fifth and sixth grooves to receive said fourth, fifth and sixth rivets respectively;

said medial hinge and said lateral hinge having concave surfaces facing the knee and opposite each other, whereby, in use, when the wearer's leg is extended, said first variable axis of rotation and said second variable axis of rotation are coincident and in alignment with the wearer's epicondyles, and when the wearer's leg flexes and extends, said first variable axis of rotation and said second axis of rotation are coincident throughout the range of motion and with the axis of rotation of the knee, thereby accurately mimicking the instantaneous axis of rotation of the wearer's knee throughout flexion and extension, abduction and adduction, internal-external rotation and anterior/posterior translation;

wherein said shank cuff further includes a slidable lower shin cuff having an anterior portion, said anterior portion of said lower shin cuff comprising a vertical slot of given length and the anterior portion of said shank cuff comprises a tongue inserted in said vertical slot, such that said tongue and slot cooperate so that said lower shin cuff slides towards and away from said hinges; whereby, in use, when a wearer's leg flexes and extends, said slidable lower shin cuff slides towards and away from said hinges to prevent the ratcheting motion caused by alternating flexion and extension, thus preventing migration of said knee orthosis along the wearer's leg.

3. The knee orthosis according to claim 2, wherein:

said first pair of parallel, concentric shells further comprises an inside shell and an outside shell, said inside shell being provided with a first extension fastened to said lateral portion of said thigh cuff and said outside shell being fastened to said inside shell;

said first shell is provided with a second extension, said second extension being fastened to said lateral portion of said shank cuff;

said second pair of parallel, concentric shells further comprises an inside shell and an outside shell, said inside shell being provided with a third extension fastened to said medial portion of said shank cuff and said outside shell being fastened to said inside shell; and said second shell is provided with a fourth extension, said fourth extension being fastened to said medial portion of said shank cuff.

4. The knee orthosis according to claim 3, wherein:

said thigh cuff further comprises means to adjust said thigh cuff to a wearer's thigh; and said shank cuff further comprises means to adjust said shank cuff to a wearer's shank.

5. The knee orthosis according to claim 4, wherein:

said means to adjust said thigh cuff to a wearer's thigh comprise:

interior and exterior thigh control bars, located on said anterior portion of said thigh cuff, including a first set of cooperating, vertically oriented teeth;

at least one horizontal groove on each of said interior and exterior thigh control bars; and at least one first plate, having at least one hole corresponding to said horizontal grooves, to lock said interior and exterior thigh control bars into position by fastening means inserted through said horizontal grooves and inside said at least one hole; and said means to adjust said shank cuff to a wearer's thigh comprise:

interior and exterior shank control bars, located on said anterior portion of said shank cuff, including a second set of cooperating, vertically oriented teeth;

at least one horizontal groove on each of said interior and exterior thigh control bars; and at least one second plate, having at least one hole corresponding to said horizontal grooves, to lock said interior and exterior shank control bars into position by fastening means inserted through said horizontal slots and inside said at least one hole.

6. The knee orthosis according to claim 5, wherein:

said lateral portion of said thigh cuff is configured to rest mainly on the vastus lateralis of the wearer's thigh; and said anterior portion of said shank cuff is configured to rest mainly on the tibial tuberosity of the wearer's shank.

7. The knee orthosis according to claim 6, wherein:

said at least one first plate is cambered for an even distribution of surface force and is made of plastic; and said at least one second plate is cambered for an even distribution of surface force and is made of plastic.

8. The knee orthosis according to claim 7, wherein said vertical slot and said tongue are selected so that the relative movement of said tongue with respect to said slot is approximately 1 cm.

9. The knee orthosis according to claim 8, further comprising stops mounted in said first, second, third, fourth, fifth and sixth slots to limit the range of motion of said knee orthosis.

* * * * *